United States Patent [19]

Sih

[11] Patent Number: 4,861,724
[45] Date of Patent: Aug. 29, 1989

[54] PROCESS FOR PREPARING OPTICALLY ACTIVE 2,2'-DIHYDROXY-1,1'-BINAPHTHYL

[75] Inventor: Charles J. Sih, Madison, Wis.

[73] Assignee: Wisconsin Alumni Research Foundation, Madison, Wis.

[21] Appl. No.: 120,248

[22] Filed: Nov. 3, 1987

Related U.S. Application Data

[63] Continuation of Ser. No. 741,066, Jun. 4, 1985, abandoned.

[51] Int. Cl.[4] ............................................. C12P 41/00
[52] U.S. Cl. .................................... 435/280; 435/136
[58] Field of Search ........................................ 435/280

[56] References Cited

PUBLICATIONS

Wu et al.-Chem. Abst. vol. 104 (1986), p. 186,099h.
Fujimoto-Chem. Abst. vol. 104 (1986) p. 105,826t,
Y. Chao, G. R. Weisman, G. D. Y. Sogah & D. J. Cram; J. American Chem. Soc., 101:17, 8/15/79; "Host-Guest Complexation.21. Catalysis and Chiral Recognition through Designed Complexation of Transition States in Transacylations of Amino Ester Salts."
Evan P. Kyba, George W. Gokel, Feike de Jong, Kenji Koga, Lynn R. Sousa, Merrell G. Siegel, Lester Kaplan, G. Dotsevi, Y. Sogah, & Donald J. Cram; The Journal of Organic Chemistry, vol. 42, No. 26, Dec. 23, 1977; "Host-Guest Complexation. 7. The Binaphthyl Structural Unit in Host Compounds."
J. Jacques, C. Fouquey, R. Viterbo; Tetrahedron Letters No. 48, pp. 4617-4620, 1971; "Enantiomeric Cyclic Binaphthyl Phosphoric Acids as Resolving Agents."
H. B. Kagan; Comprehensive Organometallic Chemistry, vol. 8, Pergamon Press, Oxford, 1982, p. 463; "Asymmetric Syntheses is Using Organometallic Catalysts."
Ryoji Noyori & Masaaki Suzuki; Angew. Chem. Int. Ed. Engl. 23 (1984) 847-876; "Prostaglandin Syntheses by Three-Component Coupling".
William H. Pirkle & James L. Schreiner; J. Org. Chem. 1981, 46, 4988-4991; "Chiral High-Pressure Liquid Chromatographic Stationary Phases. 4. Separation of the Enantiomers of Bi-β-naphthols and Analogues."
Yoshio Okamoto, Shiro Honda, Ichiro Okamoto & Heimei Yuki; J. Am. Chem. Soc. 1981, 103, 6971-6973. "Novel Packing Material for Optical Resolution: (+)-Poly(triphenylmethyl methacrylate) Coated on Macroporous Silica Gel."
R. Noyori, I. Tomino, Y. Tanimoto, & M. Nishizawa; J. Am. Chem. Soc. 1984, 106, 6709-6716; "Rational Designing of Efficient Chiral Reducing Agents. Highly Enantioselective Reduction of Aromatic Ketones by Binaphthol-Modified Lithium Aluminum Hydride Reagents."

*Primary Examiner*—Sam Rosen
*Attorney, Agent, or Firm*—Howard W. Bremer

[57] ABSTRACT

The invention provides a process for preparing optically-active 2,2'-dihydroxy-1,1'-binaphthyl by subjecting esters of (+) 2,2'-dihydroxy-1,1'-binaphthyl to the enantioselective hydrolytic enzymatic action of microorganisms of the orders Moniliales and Mucorales.

10 Claims, No Drawings

PROCESS FOR PREPARING OPTICALLY ACTIVE 2,2'-DIHYDROXY-1,1'-BINAPHTHYL

This application is a continuation of application Ser. No. 741,066, filed June 4, 1985, now abandoned.

FIELD OF THE INVENTION

The present invention relates to a process for preparing optically-active 2,2'-dihydroxy-1,1'-binaphthyl (binaphthol, 1), which are useful intermediates in asymmetric synthesis.

BACKGROUND ART

A variety of sterochemical studies have been successfully carried out using the optically-active bi-beta-naphthols (1R and 1S). For example, they can be converted into chiral crown ethers useful as stereoselective complexing agents [D. J. Cran and coworkers, *J. Am. Chem. Soc. J,* 10, 4948 (1979)]. Moreover, 1 and 2 are important chiral auxiliaries to form chiral reducing agents [R. Noyori et al., *J. Am. Chem. Soc.,* 106, 6709 (1984)]. For example, 1R and 1S complexes with LiAlH$_4$ to form chiral hydride reagent, BiNAL-H (2R and 2S), which are important in the commercial syntheses of lprostaglandins [R. Noyori and M. Suzuki, *Angew. Chemie Int. Ed.,* 23, 847 (1984)]. In addition, 1 and 2 can be converted into useful chiral catalysts for asymmetric hydrogenation (H. Kagan in G. Wilkinson, F. G. A. Stone, and E. W. Abel: *Comprehensive Organometallic Chemistry,* Vol. 8, Pergamon Press, Oxford, 1982, p. 463).

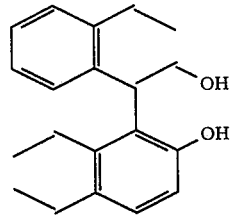
(R)-(+)-1

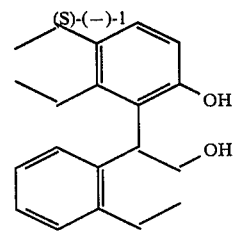
(S)-(−)-1

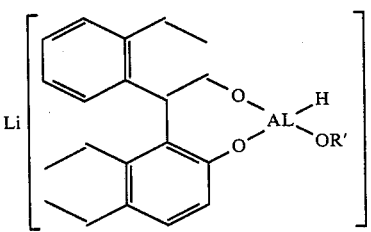
2R

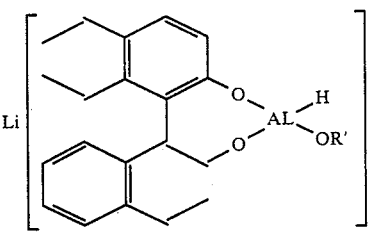
2S

Until now, 3 has been resolved only by classical means involving the tedious separation of diastereomeric derivatives [J. Jacques et al., *Tetrahedron Lett.,* 4617 (1971); D. J. Cram et al., *J. Org. Chem.,* 42, 4173 (1977)] or via chromatographic resolution upon an HPLC column packed with chiral stationary phase [W. H. Prikle and J. L. Schreiner, *J. Org. Chem.,* 46, 4988 (1981); Y. Okamoto et al., *J. Am. Chem. Soc.,* 103, 6971 (1981)].

Such methods have distinct disadvantages in that they are cumbersome to carry out, and require the use of expensive reagents. As a consequence they are costly.

DISCLOSURE OF INVENTION

The present invention relates to an improved process for producing optically-active bi-beta-naphthols 1R and 1S.

More particularly, it relates to a process for the enantioselective hydrolysis of racemic bi-beta-naphthol diacetates (3) by the action of microbial esterases.

Microorganisms which have esterase activity are well known in the microbiological art [see K. Kieslich, "Microbial Transformations of Non-Steroid Cyclic Compounds" (Georg Thieme Publishers, Stuttgart, 1976)] some of which can be used for conducting the process of the present invention. Although any of such microorganisms can be employed in the process of this invention, the genera of microorganisms specifically set forth hereinafter are particularly applicable.

The (±)-bi-beta-naphthol diacetate (3) can be incorporated in a nutrient medium of standard composition in which such organisms are cultivated and the usual conditions of fermentation can then be employed to effect the hydrolytic transformation. Alternatively, the active principle can be removed from the growing culture of the microorganism, for instance by lysis of the cells to release the enzymes, or by suspension of the resting cells in a fresh aqueous medium. To further reduce the cost of the process the cells and the enzyme may be immobilized as is well known in the art. In any of these techniques, an ester function will be selectively cleaved, so long as the active enzyme elaborated by the microorganism is present. Of course, the temperature, time and pressure conditions under which the contact of the (±)-bi-beta-naphthol diacetate (3) with the esteratic enzyme is carried out are interdependent as will be apparent to those skilled in the art. For instance, with gentle heating and at atmospheric pressure, the time required will be less than if the process progresses at room temperature under conditions otherwise the same. Of course, neither temperature, nor pressure, nor time should be so great that the substrate is degraded. Where a growing culture of the organism is being used, the process conditions should also be sufficiently gentle so that the organism is not killed before it elaborates sufficient proteolytic enzymes to permit destruction of the oxidative enzyme. Generally, at atmospheric pressure, the temperature can range from about 10° to about 35° C., and the time from about 12 hours to about 10 days. It has been observed that there are variations in the efficiency with which different orders, genera, and species of microorganisms accomplish the oxidation process of this invention. Microorganisms of the orders Mucorales and Moniliales are particularly suitable for practicing the method of this invention.

EXAMPLE 1

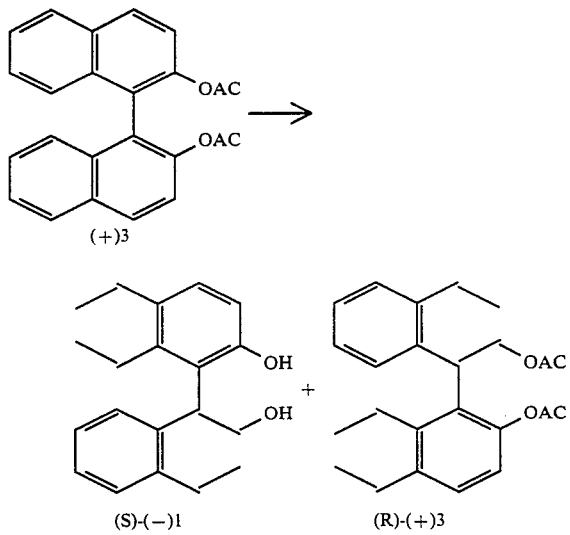

A. Fermentation

Surface growth from a one week old agar slant of *Absidia glauca* ATCC 6776A grown on agar of the following composition:

|  | Gms |
| --- | --- |
| Malt Extract | 20 |
| Glucose | 20 |
| Peptone | 1 |
| Agar | 20 |
| Distilled water, q.s. 1 liter | |
| (Sterilized 15 min at 20 p.s.i.) | | was suspended in 5 ml of an 0.85% saline solution. One ml portions of this suspension were used to inoculate a 250 ml Erlenmeyer flask (F-1stage) containing 50 ml of the following medium (Vogel):

| Vogel's medium | Gms |
| --- | --- |
| Yeast extract | 5 |
| Casamino acids | 5 |
| Dextrose | 40 |
| Na$_3$—citrate-5½H$_2$O | 3 |
| KH$_2$PO$_4$ | 5 |
| NH$_4$NO$_3$ | 2 |
| CaCl$_2$.2H$_2$O | 0.1 |
| MgSO$_4$.7H$_2$O | 0.2 |
| Trace element solution 0.1 ml | |
| Distilled water, q.s. 1 liter | |
| pH 5.6 (sterilized for 15 min at 30 p.s.i.) | |

| Trace element solution | Gm/100 ml |
| --- | --- |
| Citric acid-1H$_2$O | 5 |
| ZnSO$_4$.7H$_2$O | 7 |
| Fe[(NH$_4$)$_2$.6H$_2$O | 1 |

| -continued | |
| --- | --- |
| CuSO$_4$.5H$_2$O | 0.25 |
| MnSO$_4$.1H$_2$O | 0.05 |
| H$_3$BO$_3$ | 0.05 |
| Na$_2$MoO$_4$.2H$_2$O | 0.05 |

The flasks were incubated at 25° C. on a rotary shaker (250 cycles/min—2" radius) for 24–48 hours until visible good growth was observed, after which a 10% volume transfer was made to a 2 liter Erlenmeyer flask containing 200 ml of Vogel's medium. After incubation for 40 hours, 200 mg of (±)-bi-beta-naphthol diacetate (3) suspended in 1 ml of dimethylformamide and 0.5 ml of Tween 80 were added to the flask resulting in a final substrate concentration of 0.1%. A total of two 2-liters Erlenmeyer flasks were used. The F-2 stage flasks were then incubated for an additional 120 hours under the conditions used in the incubation of the F-1 stage flasks.

B. Isolation 56 hours after addition of the substrate, the F-2 stage was terminated by filtering the flask contents through a pad of celite to remove the mycelia. The filtrate was extracted with ethyl acetate (3×500 ml). The combined organic extracts were dried over sodium sulfate and concentrated in vacuo to give a residue (0.91 g). This residue was dissolved in 4 ml of hexane-CH$_2$Cl$_2$ (1:1) and chromatographed on a 28 g silica gel (MN Kieselgel 60, Brinkmann) column (2×45 cm). The column was eluted successively with a solvent mixture consisting of hexane-CH$_2$Cl$_2$ (400 ml of 1:1, 200 ml of 4:6; 400 ml of 35:65; and 200 ml of 3:7) and 7 ml fractions were collected. Fraction 1 (10–28) contained 135 mg of residual R-binaphthol diacetate (3R); while fraction 2 (29–80) contained 143 mg of (−)-S-binaphthol (1S) $[\alpha]_D^{25}$ −36.8° (1.0 THF); ee=>0.98 [reported: $[\alpha]_D^{20}$ −38° (c, 1.0 THF), *J. Am. Chem. Soc.*, 3129 (1979)].

C. Analysis

The progress of the microbiological hydrolysis of (±)-bi-beta-naphthol diacetate (3) can be followed by thin-layer chromatographic analyses using Brinkmann 20×20 cm (EM) plates (0.25 mm thickness) of silica gel containing PF254 indicator. The plates were developed in a solvent system consisting of CHCl$_3$-acetone (98.2) and the relative mobilities were: bi-beta-naphthol diacetate (R$_f$=0.74), and bi-beta-naphthol R$_f$=0.38), as revealed by spraying the TLC plate with a reagent consisting of: ceric sulfate (3.5%) in 2N H$_2$SO$_4$. Upon gentle heating of the TLC plate, the compounds emerge as dark brownish spots.

D. Determination of Optical Purity

The optical purity expressed an enantiomeric excess (ee) is determined by high-performance liquid chromatography using an ionically bonded chiral stationary phase as described by W. H. Pirkle and J. L. Shreiner, *J. Org. Chem.*, 46, 4988 (1981).

EXAMPLES 2–6

Oprically active (−)-S-binaphthol (1S) and (+)-R-binaphthol diacetate were prepared in accordance with the procedure of Example 1 except the following organisms were used for the enantioselective hydrolysis.
 1. *Gliocladium roseum* ATCC 10521
 2. *Phycomyces blakesleeanus* (+) ATCC 8743A 3. *Syncephalastrum sp.* NRRL M1486
4. *Rhizopus arrhizus* NRRL x213
5. *Zygorhynchus heterogamus* ATCC 42614

NRRL—Northern Regional Research Lab., Peoria, Ill.

ATCC—American Type Culture Collection, Rockville, Md

Although in the foregoing Examples the diacetate ester of (+)-2,2′-dihydroxy-1,1′-binaphthyl is used as the substrate, other esters of that compound, for example, the propionic or butyric esters, can be used with comparable results.

I claim:

1. A process for preparing optically active 2,2′-dihydroxy-1,1′-binaphthyl, which comprises subjecting esters of (+)-2,2′-dihydroxy-1,1′-binaphthyl to the enantio-selective hydrolytic enzymatic action of microorganisms of the orders Moniliales and Mucorales and recovering the desired optically-active compound from the reaction mixture.

2. A process in accordance with claim 1 wherein the microorganism is selected from the group consisting of *Absidia glauca* ATCC 6776A, *Gliocladium roseum* ATTC 10521, *Phycomyces blakesleeanus* (+) ATCC 8743A, Syncephalastrum sp. NRRL M1486, *Rhizopus arrhizus* NRRL x 213 and *Zygorhynchus heterogamus* ATTC 42614 and recovering optically active 2,2′-dihydroxy-1,1′-binaphthyl from the reaction mixture.

3. A process in accordance with claim 2 wherein the the enantio-selective hydrolytic enzymatic action is effected using immobilized cells of the microorganism.

4. The process in accordance with claim 2 wherein the the enantio-selective hydrolytic enzymatic action is effected using an immobilized enzyme from the microorganism.

5. The method of claim 2 wherein the microorganism is *Absidia glauca* ATCC 6776A.

6. The method of claim 2 wherein the microorganism is *Gliocladium roseum* ATCC 10521.

7. The method of claim 2 wherein the microorganism is *Phycomyces blakesleeanus* (+) ATCC 8743A.

8. The method of claim 2 wherein the microorganism is Syncephalastrum sp NRRL M1486.

9. The method of claim 2 wherein the microorganism is *Rhizopus arrhizus* NRRL x213.

10. The method of claim 2 wherein the microorganism is *Zygorhynchus heterogamus* ATCC 42614.

* * * * *